(12) United States Patent
Mori et al.

(10) Patent No.: US 10,737,117 B2
(45) Date of Patent: Aug. 11, 2020

(54) MEDICAL APPARATUS AND METHOD

(71) Applicant: Toshiba Energy Systems & Solutions Corporation, Kawasaki-shi (JP)

(72) Inventors: Shinichiro Mori, Chiba (JP); Keiko Okaya, Setagaya (JP); Ryusuke Hirai, Shinagawa (JP); Koki Yanagawa, Tokorozawa (JP); Fumi Maruyama, Miura (JP); Yasushi Iseki, Yokohama (JP)

(73) Assignee: Toshiba Energy Systems & Solutions Corporation, Kawasaki-shi (JP)

( * ) Notice: Subject to any disclaimer, the term of this patent is extended or adjusted under 35 U.S.C. 154(b) by 0 days.

(21) Appl. No.: 16/223,579

(22) Filed: Dec. 18, 2018

(65) Prior Publication Data
US 2019/0184200 A1 Jun. 20, 2019

(30) Foreign Application Priority Data
Dec. 20, 2017 (JP) ................. 2017-244071

(51) Int. Cl.
*A61N 5/10* (2006.01)
*A61B 6/00* (2006.01)

(52) U.S. Cl.
CPC ......... *A61N 5/1049* (2013.01); *A61N 5/1037* (2013.01); *A61N 5/1065* (2013.01); *A61B 6/487* (2013.01); *A61B 6/5223* (2013.01); *A61B 6/5288* (2013.01); *A61N 5/1069* (2013.01);*A61N 2005/1059* (2013.01); *A61N 2005/1061* (2013.01);
(Continued)

(58) Field of Classification Search
CPC .. A61N 5/1049; A61N 5/1037; A61N 5/1065; A61N 2005/1061;
(Continued)

(56) References Cited

U.S. PATENT DOCUMENTS 8,638,982 B2 1/2014 Shin et al.
9,155,909 B2 * 10/2015 Ishikawa .............. A61N 5/1049
(Continued)

FOREIGN PATENT DOCUMENTS

JP 2017-35204 A 2/2017
JP 2017-144000 8/2017

*Primary Examiner* — Kiho Kim
(74) *Attorney, Agent, or Firm* — Oblon, McClelland, Maier & Neustadt, L.L.P.

(57) ABSTRACT

A medical apparatus according to an embodiment includes an acquirer, an identifier, an output controller, a display controller, and an input operation acquirer. The acquirer acquires a fluoroscopic image of a object from an imager which performs imaging by irradiating the object with an electromagnetic wave to generate the fluoroscopic image. The identifier identifies a target position of the object in the fluoroscopic image. The output controller outputs an irradiation permission signal to a therapeutic device which irradiates the object with a therapeutic beam when the target position identified by the identifier is settled within an irradiation permission range. The display controller causes a display to display an interface image for receiving an instruction to start each of a preparation stage of a therapy and an irradiation stage of the therapeutic beam. The input operation acquirer acquires details of an input operation performed by a user in the interface image.

15 Claims, 8 Drawing Sheets

(52) U.S. Cl.
CPC ............... *A61N 2005/1062* (2013.01); *A61N 2005/1072* (2013.01); *A61N 2005/1074* (2013.01); *A61N 2005/1087* (2013.01)

(58) Field of Classification Search
CPC .... A61N 2005/1074; A61N 2005/1062; A61N 2005/1072; A61N 2005/1087; A61N 2005/1059; A61N 5/1069; A61B 6/487; A61B 6/5288; A61B 6/5223
See application file for complete search history.

(56) References Cited

U.S. PATENT DOCUMENTS

| | | | |
|---|---|---|---|
| 9,724,049 B2 * | 8/2017 | Umekawa | A61B 6/541 |
| 2005/0053267 A1 | 3/2005 | Mostafavi | |
| 2006/0182326 A1 | 8/2006 | Schildkraut et al. | |
| 2013/0343511 A1 | 12/2013 | Shukla et al. | |
| 2014/0343401 A1 | 11/2014 | Huber et al. | |
| 2015/0087881 A1 * | 3/2015 | Miyamoto | A61N 5/1049 600/1 |
| 2015/0335919 A1 * | 11/2015 | Behar | A61B 6/0492 606/27 |
| 2016/0082284 A1 | 3/2016 | Ooga et al. | |
| 2016/0302747 A1 * | 10/2016 | Averbuch | A61B 34/20 |
| 2017/0197098 A1 * | 7/2017 | Hirasawa | A61B 6/00 |
| 2017/0231586 A1 | 8/2017 | Hirai et al. | |
| 2017/0251992 A1 * | 9/2017 | Jang | A61B 6/0457 |
| 2018/0160990 A1 * | 6/2018 | Weingarten | A61B 6/12 |
| 2018/0263706 A1 * | 9/2018 | Averbuch | A61B 17/00234 |
| 2019/0026584 A1 * | 1/2019 | Hirai | A61N 5/1049 |
| 2020/0016432 A1 * | 1/2020 | Maolinbay | A61N 5/1047 |

* cited by examiner

MEDICAL APPARATUS AND METHOD

CROSS-REFERENCE TO RELATED APPLICATION

This application is based upon and claims the benefit of priority from Japanese Patent Application No. 2017-244071 filed on Dec. 20, 2017; the entire content of which is incorporated herein by reference.

BACKGROUND OF THE INVENTION

Field of the Invention

Embodiments described herein relate generally to a medical apparatus and a method.

Description of Related Art

Therapeutic devices which irradiate a patient (object) with a therapeutic beam such as a heavy particle beam or a radiation are known. There are cases in which a lesion of a object, that is, a spot to be irradiated with a therapeutic beam moves due to respirations, heartbeat, intestinal movements, and the like. As a therapeutic method suitable therefor, a gated irradiation method and a tracking irradiation method are known.

When a lesion which moves due to respirations is irradiated with a therapeutic beam, there is a need to perform irradiation synchronously with respiratory phases of a object. Techniques of respiratory phase synchronization include a technique of ascertaining the respiratory phase (external respiratory synchronization) by utilizing output values of various sensors attached to the body of a object, and a technique of ascertaining the respiratory phase (internal respiratory synchronization) based on a fluoroscopic image of a object. The processing for respiratory phase synchronization is performed by a medical apparatus which outputs a control signal to a therapeutic device. For example, a medical apparatus controls a therapeutic device by performing wired or wireless communication with the therapeutic device.

For example, a therapy of this kind is performed in a divided into a plurality of stages, such as a planning stage, a preparation stage, and a therapy stage. Here, if processing in various stages performed by a medical apparatus is not sufficiently supported, a work load of a physician or a nurse may increase, or a physical load may be applied to a object. However, in technologies in the related art, there have been cases in which a therapy cannot be comprehensively supported through internal respiratory synchronization.

SUMMARY OF THE INVENTION

An object to be achieved by the present invention is to provide a medical apparatus and method, which is capable of comprehensively supporting a therapy through internal respiratory synchronization.

A medical apparatus according to an embodiment includes an acquirer, an identifier, an output controller, a display controller, and an input operation acquirer. The acquirer acquires a fluoroscopic image of a object from an imager which performs imaging by irradiating the object with an electromagnetic wave to generate the fluoroscopic image. The identifier identifies a target position of the object in the fluoroscopic image. The output controller outputs an irradiation permission signal to a therapeutic device which irradiates the object with a therapeutic beam when the target position identified by the identifier is settled within an irradiation permission range. The display controller causes a display to display an interface image for receiving an instruction to start each of a preparation stage of a therapy and an irradiation stage of the therapeutic beam. The input operation acquirer acquires details of an input operation performed by a user in the interface image.

According to the present embodiment, it is possible to provide a medical apparatus and method, which is capable of comprehensively supporting a therapy through internal respiratory synchronization.

DETAILED DESCRIPTION OF THE INVENTION

Hereinafter, a medical apparatus and a method according to an embodiment will be described with reference to the drawings. In this application, the expression "based on XX" denotes "based on at least XX" and also includes a case based on another element in addition to XX. The expression "based on XX" is not limited to a case of directly adopting XX and also includes a case based on a result realized by performing computation or processing with respect to XX. The term "XX" indicates an arbitrary element (for example, arbitrary information).

<Configuration>

Figure 1:
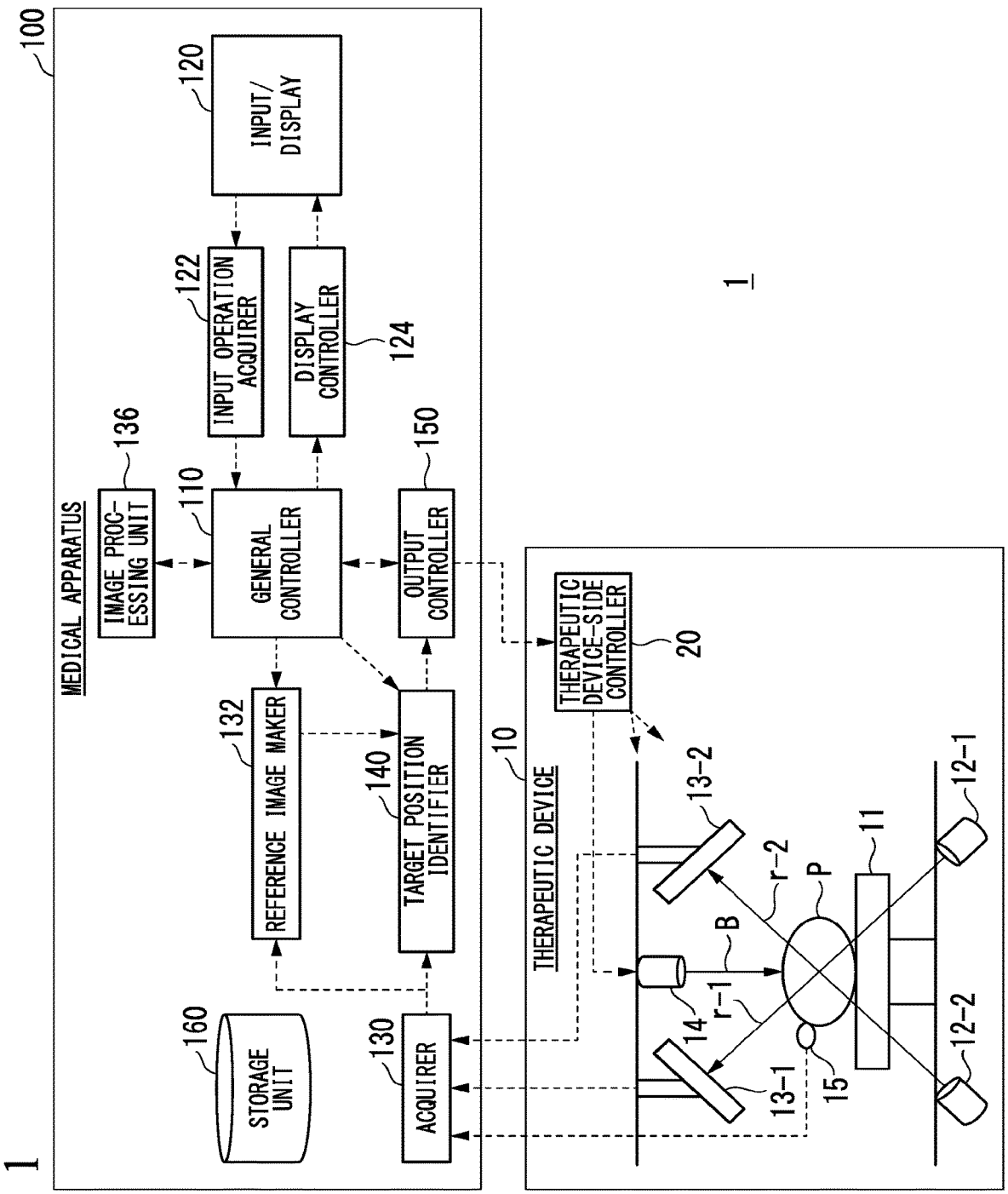
FIG. 1 is a configuration diagram of a therapy system including a medical apparatus.

FIG. 1 is a configuration diagram of a therapy system 1 including a medical apparatus 100. For example, the therapy system 1 includes a therapeutic device 10 and the medical apparatus 100.

For example, the therapeutic device 10 includes a bed 11, radiation sources 12-1 and 12-2, detectors 13-1 and 13-2, an irradiation gate 14, a sensor 15, and a therapeutic device-side controller 20. Hereinafter, a hyphen and a numeral following it in the reference sign indicate a fluoroscopic radiation or a fluoroscopic image realized by a set of a radiation source and a detector. Suitably, the hyphen and the numeral following it in the reference sign may be omitted in description.

A object P to be treated is fixed to the bed 11. The radiation source 12-1 irradiates the object P with a radiation r-1. The radiation source 12-2 irradiates the object P with a radiation r-2 at an angle different from that of the radiation source 12-1. The radiations r-1 and r-2 are examples of electromagnetic waves and are X-rays, for example. Hereinafter, description will be given on this premise.

The radiation r-1 is detected by the detector 13-1, and the radiation r-2 is detected by the detector 13-2. For example, the detectors 13-1 and 13-2 are flat panel detectors (FPD), image intensifiers, or color image intensifiers. The detector 13-1 detects energy of the radiation r-1, performs digital conversion, and outputs the conversion result to the medical apparatus 100 as a fluoroscopic image TI-1. The detector 13-2 detects energy of the radiation r-2, performs digital conversion, and outputs the conversion result to the medical apparatus 100 as a fluoroscopic image TI-2. In FIG. 1, two sets of the radiation source and the detector are illustrated. However, the therapeutic device 10 may include three or more sets of the radiation source and the detector.

In a therapy stage, the irradiation gate 14 irradiates the object P with a therapeutic beam B. Examples of the therapeutic beam B include a heavy particle beam, an X-ray, a y-ray, an electron beam, a proton beam, and a neutron beam. In FIG. 1, only one irradiation gate 14 is illustrated. However, the therapeutic device 10 may include a plurality of irradiation gates.

The sensor 15 is provided to recognize an external respiratory phase of the object P and is attached to the body of the object P. For example, the sensor 15 is a pressure sensor.

The therapeutic device-side controller 20 operates the radiation sources 12-1 and 12-2, the detectors 13-1 and 13-2, and the irradiation gate 14 in response to a control signal from the medical apparatus 100.

For example, the medical apparatus 100 includes a general controller 110, an input/display 120, an input operation acquirer 122, a display controller 124, an acquirer 130, a reference image maker 132, an image processor 136, a target position identifier 140, an output controller 150, and a storage 160. For example, at least a part of each of the general controller 110, the input operation acquirer 122, the display controller 124, the acquirer 130, the reference image maker 132, the image processor 136, the target position identifier 140, and the output controller 150 is realized by a hardware processor such as a central processing unit (CPU) or a graphics processing unit (GPU) executing a program (software) stored in the storage 160. A part or all of these constituent elements may be realized by hardware (circuit section; including circuitry) such as a large scale integration (LSI), an application specific integrated circuit (ASIC), or a field-programmable gate array (FPGA) or may be realized by cooperation of software and hardware.

Hereinafter, the function of each part of the medical apparatus 100 will be described. In description of the medical apparatus 100, unless otherwise identified, processing performed with respect to the fluoroscopic image TI will be regarded to be executed in parallel with both the fluoroscopic images TI-1 and TI-2. The general controller 110 generally controls the functions of the medical apparatus 100.

For example, the input/display 120 includes a display device such as a liquid crystal display (LCD), an organic electroluminescence (EL) display device, or a light emitting diode (LED) display; and an input device which receives an input operation performed by an operator. The input/display 120 may be a touch panel in which a display device and an input device are integrally formed or may include an input device such as a mouse and a keyboard.

The input operation acquirer 122 recognizes the details of an operation (touching, flicking, swiping, clicking, dragging, key-inputting, or the like) performed with respect to the input/display 120 and outputs the details of the recognized operation to the general controller 110. The display controller 124 causes the input/display 120 to display an image in response to an instruction from the general controller 110. The display controller 124 causes the input/display 120 to display an interface screen for receiving an instruction to start each of a preparation stage of a therapy and an irradiation stage of the therapeutic beam B. Displaying of an image includes generation of elements of an image performed based on a computation result and allocation of elements of an image made in advance to a display screen.

The acquirer 130 acquires the fluoroscopic image TI from the therapeutic device 10. The acquirer 130 acquires a detection value of the sensor 15. The acquirer 130 acquires three-dimensional volume data of the object P from a medical inspection device (not illustrated). When the fluoroscopic image TI is used as a reference image to identify the position of a target, the reference image maker 132 generates a reference image to be used for identifying a target position, based on the fluoroscopic image TI acquired by the acquirer 130. These will be described below in detail.

The image processor 136 performs image processing such as deformable registration and a digitally reconstructed radiograph (DRR) image generation. Deformable registration is processing performed with respect to time-series three-dimensional volume data, in which positional information designated for three-dimensional volume data at a certain point of time is deployed in three-dimensional volume data at another point of time. A DRR image is a virtual fluoroscopic image generated by irradiating three-dimensional volume data with a radiation from a virtual radiation source.

The target position identifier 140 identifies the position of a target in the fluoroscopic image TI. A target position may be a lesion of the object P, that is, a position to be irradiated with the therapeutic beam B, or may be a marker or a characteristic spot of the object P. Since the difference between a characteristic spot such as the diaphragm, the heart, or a bone and surrounding spots appears in a relatively clear manner in the fluoroscopic image TI, the characteristic spot is a spot of which the position can be easily identified when a computer analyzes the fluoroscopic image TI. The target position may be one point or a region having a two-dimensional or three-dimensional spread.

The output controller 150 outputs an irradiation permission signal to the therapeutic device 10 based on the target position identified by the target position identifier 140. For example, in a gated irradiation method, when the target position is settled within a gating window, the output controller 150 outputs a gate-on signal to the therapeutic device 10. A gating window is a region set in a two-dimensional plane or a three-dimensional space and is an example of an irradiation permission range. A gate-on signal is a signal for instructing an operator to irradiate the object P with the therapeutic beam B and is an example of an irradiation permission signal. Hereinafter, description will be given on these premises. The therapeutic device 10 performs irradiation of the therapeutic beam B when a gate-on signal is input, and does not perform irradiation of the therapeutic beam B when no gate-on signal is input. The irradiation permission range is not limited to a fixedly set range and may be a range which moves in a manner following a movement of a lesion.

For example, the storage 160 is realized by a random access memory (RAM), a read only memory (ROM), a hard disk drive (HDD), or a flash memory. The storage 160 stores time-series three-dimensional CT images (hereinafter, 4D CT images), the fluoroscopic image TI, an output value of the sensor 15, and the like, in addition to the program described above.

<Flow of Therapy (Mode 1)>

Hereinafter, a flow of a therapy of the therapy system 1 will be described. For example, the therapy system 1 can perform a therapy by switching between three modes, such as markerless tracking and marker tracking which are internal respiratory synchronization, and external respiratory synchronization. Hereinafter, markerless tracking will be referred to as Mode 1, marker tracking will be referred to as Mode 2, and external respiratory synchronization will be referred to as Mode 3. Here, Mode 1 will be described. Markerless tracking includes a technique of using a template matching method or machine learning. Hereinafter, markerless tracking using the template matching method will be described, and description will be given such that the gated irradiation method is employed as an irradiation method. The medical apparatus 100 may be switchable between the template matching method and a technique using machine learning.

[Planning Stage]

In a planning stage of Mode 1, first, CT imaging of the object P is performed. In CT imaging, images of the object P are captured in various directions for each of various respiratory phases. Next, 4D CT images are generated based on the results of the CT imaging. 4D CT images are n three-dimensional CT images (an example of the three-dimensional volume data described above) arranged in time series. A period obtained by multiplying this number n by the time interval between the time-series images is set to cover a period in which the respiratory phase changes by one cycle, for example 4D CT images are stored in the storage 160.

Next, a physician, a radiologist, or the like inputs a contour with respect to one CT image of n CT images, for example. This contour is a contour of a tumor which is a lesion or a contour of an organ which is not intended to be irradiated with the therapeutic beam B. Next, for example, the image processor 136 sets the contour for each of n CT images through deformable registration. Next, a therapeutic plan is decided. A therapeutic plan is a plan for regulating irradiation of the place, the direction, and the quantity of the therapeutic beam B in accordance with the position of a lesion based on information of the set contour. The therapeutic plan is decided in accordance with a therapeutic method such as the gated irradiation method or a tracking irradiation method. A part or all of the processing in the planning stage may be executed by an external device. For example, processing of generating 4D CT images may be executed by a CT device.

Here, a region defined by the contour of a tumor, the center of gravity in this region, the position of a characteristic spot of the object P, or the like becomes a target position. Moreover, in the therapeutic plan, the position which may be irradiated with the therapeutic beam B is decided as a target position. When the contour is set through deformable registration, a margin is automatically or manually set for the target position, and a gating window is set by applying the margin. This margin is provided to absorb an error in the device, positioning, and the like.

[Positioning Stage]

In a positioning stage, the bed position is adjusted. The object P is laid on the bed 11 and is fixed by using a shell or the like. First, the bed position is roughly adjusted. In this stage, a worker visually checks for the position and the posture of the object P and moves the bed 11 to a position at which the object P will be irradiated with the therapeutic beam B from the irradiation gate 14. Accordingly, the position of the bed 11 is roughly adjusted. Next, an image to be utilized for minutely adjusting the bed position is captured. For example, when 3D-2D registration is performed, the fluoroscopic image TI is captured. For example, the fluoroscopic image TI is captured at the timing of the end of exhalation of the object P. Since the position of the bed 11 has already been roughly adjusted, an area near a lesion of the object P is imaged in the fluoroscopic image TI.

When 3D-2D registration is performed, in this stage, a DRR image is generated from three-dimensional volume data by using the radiation sources 12-1 and 12-2, the detectors 13-1 and 13-2, and the therapeutic plan information of the object P. The movement amount of the bed is calculated based on the DRR image and the fluoroscopic image TI, and the bed 11 is moved. The position of the bed 11 is minutely adjusted by repeating capturing the fluoroscopic image TI, calculating the movement amount of the bed, and moving the bed 11.

[Preparation Stage (Part 1)]

When the positioning stage ends, the processing shifts to the preparation stage. First, a DRR image of each phase is made from 4D CT images. The DRR image may be made at any time after the 4D CT images have been captured. In this case, a position, at which the gating window set in the therapeutic plan is projected, is set as the gating window on the DRR image. In the preparation stage, first, capturing the fluoroscopic image TI for making a reference image is performed. For example, the fluoroscopic image TI is captured such that two respirations of the object P are covered. While the object P performs deep respirations, an external respiratory waveform of the object P is acquired synchronously with the fluoroscopic image TI. The display controller 124 causes the input/display 120 to display the acquired external respiratory waveform. A tracking value based on the respiratory phase of the object P obtained from the external respiratory waveform is associated with the captured fluoroscopic image TI.

In this stage, the relationship between the fluoroscopic image TI and the target position is learned from information of the DRR image and the target position on the DRR image. Moreover, correction of the target position by a physician is received. From the fluoroscopic image TI in which the target position has been learned, one or more templates (reference images) are selected based on the tracking value. A template may be a cut-out characteristic part of this fluoroscopic image TI. Learning of the target position may be performed at any timing during a period from the planning stage to the therapy stage. For example, when a template is made from the fluoroscopic image TI for one respiration of the first half of the fluoroscopic images TI for two respirations of the object P, whether a target can be tracked with the fluoroscopic image TI for one respiration of the second half may be checked by using the template. In this case, the display controller 124 may cause the gating window set on the DRR image to be displayed on the fluoroscopic image TI.

[Preparation Stage (Part 2)]

Capturing the fluoroscopic image TI is restarted. The target position identifier 140 performs matching of the template with respect to the fluoroscopic images TI input in time series and allocates the target position with respect to the fluoroscopic image TI. While causing the input/display 120 to display the fluoroscopic images TI as a moving image, the display controller 124 causes the target position to be displayed in a manner of being superimposed on a frame of the fluoroscopic image TI in which the target position is allocated. As a result, the tracking results of the target position are checked by a physician or the like.

In this case, the display controller 124 causes the gating window set on the DRR image to be displayed on the fluoroscopic image TI. The output controller 150 determines whether or not the target position is settled within the gating window, regarding both the fluoroscopic images TI-1 and TI-2. In the therapy stage, a gate-on signal is output to the therapeutic device 10 when the target position is settled within the gating window. However, in the preparation stage, the presence or absence of an output of a gate-on signal is transmitted to the display controller 124 via the general controller 110. The display controller 124 causes the input/display 120 to display the presence or absence of an output of a gate-on signal in parallel with displaying of the moving image. As a result, the output timing of a gate-on signal is checked by a physician or the like.

[Therapy Stage]

In the therapy stage, the output controller 150 outputs a gate-on signal to the therapeutic device 10 when the target position is settled within the gating window, regarding both the fluoroscopic images TI-1 and TI-2. Accordingly, a therapy is performed by irradiating a lesion of the object P with the therapeutic beam B. In the case in which the target position is the position of a lesion, irradiation of the therapeutic beam B is performed when the tracked target position is settled within the gating window. In the case in which the target position is the position of a characteristic spot of the object P, irradiation of the therapeutic beam B is performed when the position of a lesion derived out from the target position is settled within the gating window, based on the relationship between the target position learned in advance and the position of a lesion. A portion at the position of a lesion may be irradiated with the therapeutic beam B by these complex techniques. That is, irradiation of the therapeutic beam B may be performed when a lesion is settled within a first gating window and a characteristic spot is settled within a second gating window, by setting each of the position of a lesion and the position of a characteristic spot as the target position.

<Display Image and Flowchart (Mode 1)>

Hereinafter, processing of the medical apparatus 100 for supporting the flow of a therapy described above will be described.

Figure 2:
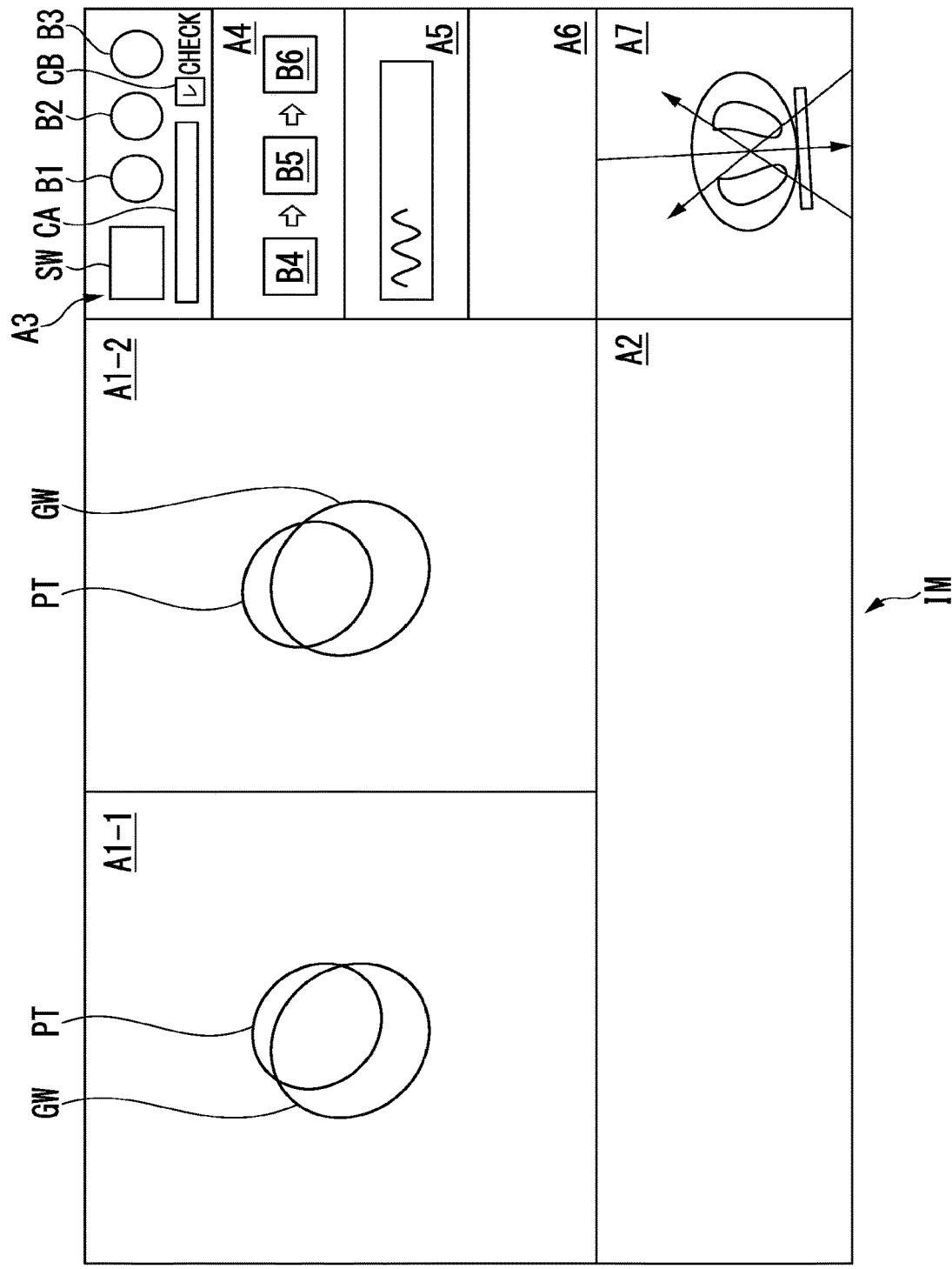
FIG. 2 is a view illustrating an example of an interface image displayed by an input/display of the medical apparatus.

FIG. 2 is a view illustrating an example of an interface image IM which is displayed by the input/display 120 of the medical apparatus 100. For example, the interface image IM includes regions A1-1, A1-2, A2, A3, A4, A5, A6, and A7.

In the region A1-1, a gating window GW or a target position PT is displayed in a manner of being superimposed on the fluoroscopic image TI-1. In the region A1-2, the gating window GW or the target position PT is displayed in a manner of being superimposed on the fluoroscopic image TI-2. In the region A2, various graphs and the like are displayed.

In the region A3, a selection window SW for receiving selection of a mode and the like, a first button B1 for instructing the therapeutic device 10 to start capturing or stop capturing the fluoroscopic image TI, a second button B2 for instructing the therapeutic device 10 to temporarily stop capturing the fluoroscopic image TI, a third button B3 for instructing the therapeutic device 10 to end a therapeutic session, a slide bar for tracing back and checking for DRR images or the fluoroscopic images TI in time series, a control area CA in which a frame advancing switch and the like are set, a check box CB for checking for completion of the preparation stage, and the like are set. For example, an operation with respect to each part of the interface image IM is performed by performing a touching operation, clicking a mouse, operating a keyboard, or the like. For example, the first button B1 is operated by performing a touching operation or clicking a mouse.

In the region A4, a fourth button B4, a fifth button B5, and a sixth button B6 for instructing the therapeutic device 10 that the therapy stage corresponding to the mode proceeds to a next step are set. In the region A5, the graph of the external respiratory waveform based on the output value of the sensor 15, and the like are displayed. In the region A6, an image indicating the therapeutic plan information of the object P, and text information are displayed. In the region A7, the irradiation direction of an X-ray, the irradiation field, the irradiation direction of the therapeutic beam B, the contour of a target, the marker ROI, and the like are displayed in a manner of being superimposed on a cross section of a CT image of the object P.

Figure 3:
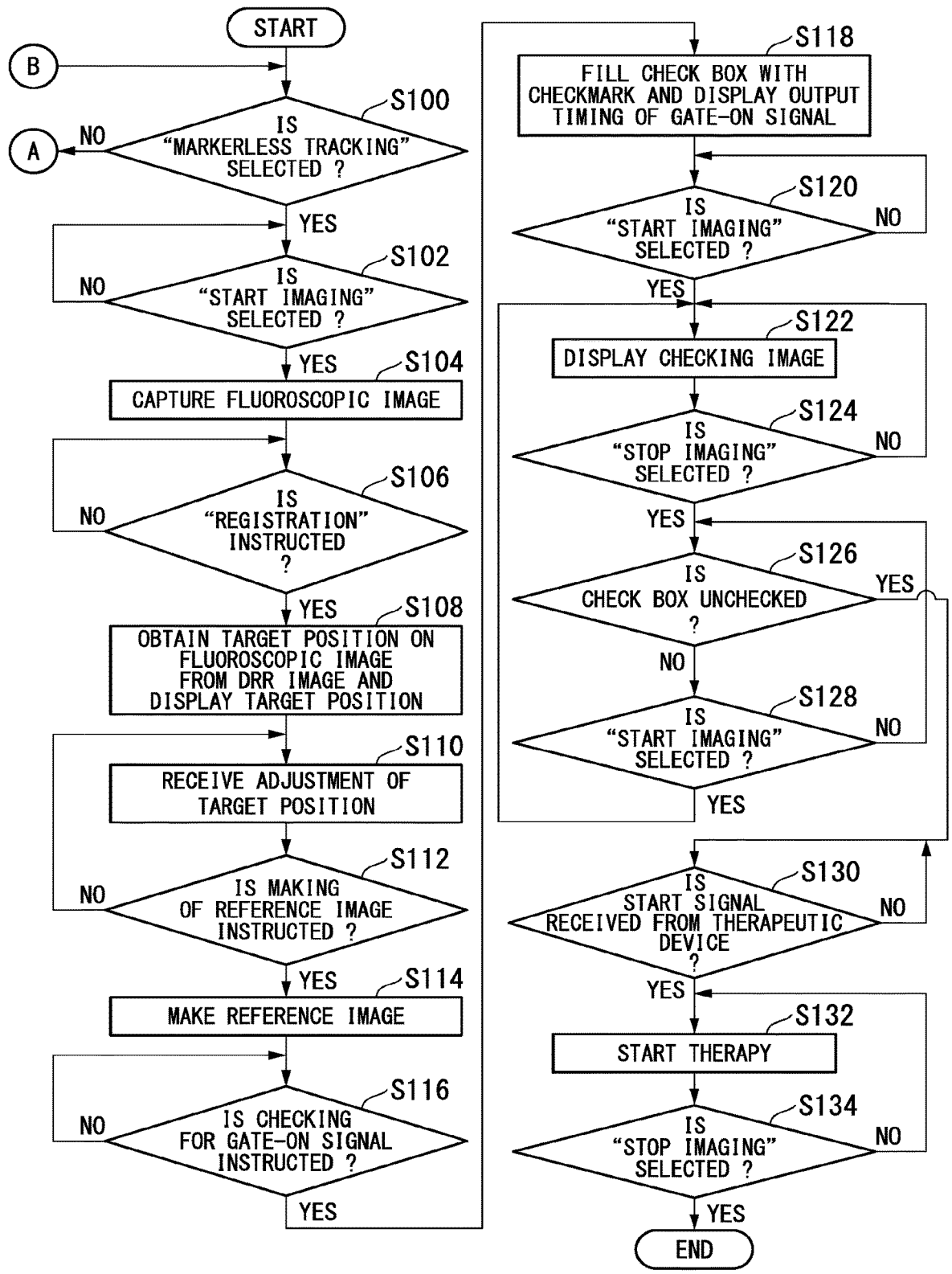
FIG. 3 is a flowchart (Part 1) illustrating an example of a flow of processing executed by the medical apparatus.

Hereinafter, various functions of the interface image IM will be described with reference to the flowchart. FIG. 3 is a flowchart (Part 1) illustrating an example of a flow of processing executed by the medical apparatus 100. First, with reference to information input from the input operation acquirer 122, the general controller 110 determines whether or not markerless tracking is selected in the selection window SW (Step S100). Selection of markerless tracking may be performed through an operation of a physician or the like, may be automatically performed in response to a signal from the therapeutic device 10, or may be automatically performed by the medical apparatus 100 based on the details of the therapeutic plan. A case in which a mode other than markerless tracking is selected will be described below. In the following description, when it is detected that an operation has been performed with respect to the medical apparatus 100, the general controller 110 is regarded to perform determination with reference to information input from the input operation acquirer 122, and description for each case will be omitted.

Figure 4:
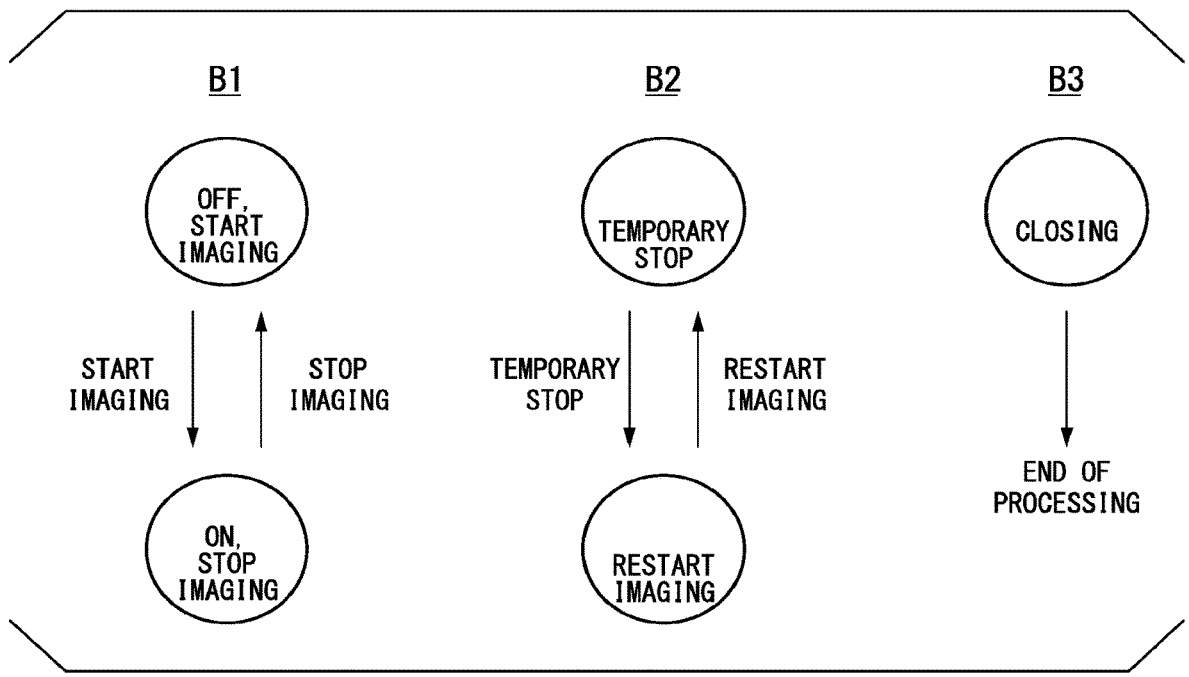
FIG. 4 is a view illustrating a change in a form of displaying a first button, a second button, and a third button.

When markerless tracking is selected in the selection window SW, the general controller 110 determines whether or not start imaging is selected by operating the first button B1 (Step S102). FIG. 4 is a view illustrating a change in a form of displaying the first button B1, the second button B2, and the third button B3. As illustrated in the diagram, in an initial state, the first button B1 indicates a state in which imaging is "OFF", that is, stopped in a form of receiving an instruction for "start imaging". When the first button B1 is operated, a state in which imaging is "ON", that is, executed is indicated, and the first button 131 changes into a form of receiving an instruction for "stop imaging". The first button B1 performs state transition between these two forms.

In an initial state, the second button B2 is in a form of receiving an instruction for "temporary stop" of imaging when being operated. When being operated, the second button B2 changes into a form of receiving an instruction for "restart imaging". In an initial state, the third button B3 is in a form of receiving an instruction for "closing" of the interface image IM. When the third button B3 is operated, the interface image IM is stopped being displayed, and a series of processing ends.

When start imaging is selected by operating the first button B1, the general controller 110 instructs the output controller 150 to instruct the therapeutic device 10 to capture the fluoroscopic image TI which becomes a template (Step S104). For example, the output controller 150 instructs the therapeutic device 10 to capture the fluoroscopic images TI fork times of respirations. The output controller 150 may output an instruction for ending imaging to the therapeutic device 10 when the first button B1 is operated again. In this manner, the output controller 150 outputs an instruction for an operation to the imager (the radiation sources 12-1 and 12-2, and the detectors 13-1 and 13-2) of the therapeutic device 10 in accordance with the details of the input operation acquired by the input operation acquirer 122. Accordingly, the medical apparatus 100 can manage an operation of the therapy system 1 including the therapeutic device 10 in an integrated manner, so that convenience is improved.

Figure 5:
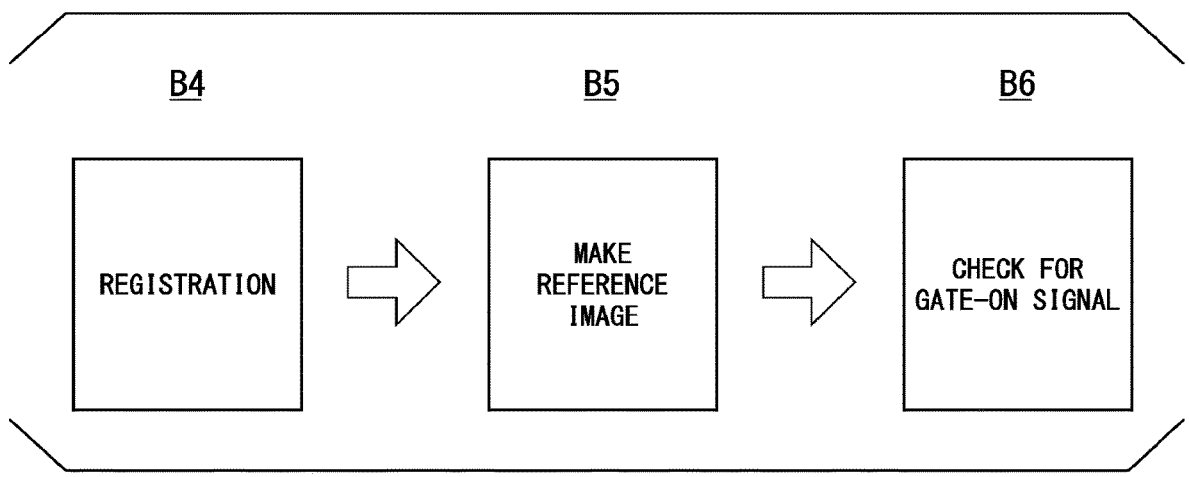
FIG. 5 is a view illustrating details of a fourth button, a fifth button, and a sixth button in Mode 1.

Next, the general controller 110 determines whether or not registration is instructed by operating the fourth button B4 (Step S106). FIG. 5 is a view illustrating details of the fourth button B4, the fifth button B5, and the sixth button B6 in Mode 1. In Mode 1, the fourth button B4 receives an instruction for registration (learning of the target position PT in the fluoroscopic image TI), the fifth button B5 receives an instruction for making a reference image, and the sixth button B6 receives an instruction for checking for a gate-on signal.

When registration is instructed by operating the fourth button B4, the general controller 110 instructs the image processor 136 to obtain a target position in the fluoroscopic image TI from the target position PT in a DRR image, and instructs the display controller 124 to cause the input/display 120 to display the obtained target position PT in a manner of being superimposed on the fluoroscopic image TI (Step S108). As described above, the image processor 136 performs processing of matching characteristic portions in images between the DRR image of which the target position PT is already known and the fluoroscopic image TI, based on the DRR image made from a CT image captured in the planning stage, or the fluoroscopic image TI captured after the planning stage, thereby deriving out the target position PT in the fluoroscopic image TI. The relationship between the fluoroscopic image TI and the target position PT is provided for the reference image maker 132. An image in which the target position PT is superimposed on the fluoroscopic image TI is displayed in the regions A1-1 and A1-2 of the interface image IM, for example. In this state, the general controller 110 receives an adjustment of the target position PT (Step S110). For example, the target position PT is adjusted by performing a drag/drop operation with respect to the regions A1-1 and A1-2. When the target position PT is adjusted, the general controller 110 provides the adjusted relationship between the fluoroscopic image TI and the target position PT for the reference image maker 132.

Next, the general controller 110 determines whether or not making a reference image is instructed by operating the fifth button B5 is instructed (Step S112). When the fifth button B5 is operated, the general controller 110 instructs the reference image maker 132 to select the fluoroscopic image TI to be used as a reference image and to perform processing such as resizing, thereby making a reference image (Step S114). The reference image maker 132 makes a reference image (template) with which the target position PT is associated and causes the storage 160 to store the reference image.

Next, the general controller 110 determines whether or not checking for a gate-on signal is instructed by operating the sixth button B6 (Step S116). When checking for a gate-on signal is instructed, the general controller 110 instructs the display controller 124 to change the check box CB into a state filled with checkmark and causes the input/display 120 to display the output timing of a gate-on signal (Step S118). In the state in which the check box CB is filled with checkmark, the output timing of a gate-on signal is calculated and displayed, but a gate-on signal is not actually output to the therapeutic device 10.

Next, the general controller 110 determines whether or not start imaging is selected by operating the first button B1 (Step S120). When start imaging is selected by operating the first button B1, the general controller 110 instructs the output controller 150 to instruct the therapeutic device 10 to capture the fluoroscopic image TI and instructs the display controller 124 to cause the input/display 120 to display a checking image using the captured fluoroscopic image TI (Step S122).

The checking image is displayed in the regions A1-1 and A1-2. The checking image is an image in which the target position PT or the gating window GW is superimposed on the fluoroscopic image TI which is reproduced as a moving image (refer to FIG. 2). The output controller 150 outputs a gate-on signal to the display controller 124, which displays the gate-on signal in the region A2 when the target position PT is settled in the gating window GW. A physician or the like can check for whether or not the target position PT such as a lesion of the object P is recognized as a correct position, whether or not the timing the target position PT is settled in the gating window GW is appropriate, the output efficiency of a gate-on signal, and the like, by visually recognizing this checking image. The checking image is displayed until stop imaging is selected by operating the first button B1 (Step S124). Even after stop imaging is selected, the checking image can be traced back and checked for by operating the control area CA in which the slide bar, the frame advancing switch, and the like are set.

When stop imaging is selected by operating the first button B1, the general controller 110 determines whether or not checkmark of the check box CB is canceled (Step S126). When checkmark of the check box CB is not canceled, the general controller 110 determines whether or not start imaging is selected by operating the first button B1 (Step S128). When start imaging is selected, the processing returns to Step S122, and when start imaging is not selected, the processing returns to Step S126. When checkmark of the check box CB is canceled, the general controller 110 determines whether or not a start signal is received from the therapeutic device 10 (Step S130). This start signal is a signal output when the therapeutic device 10 can start a therapy by operating a switch (not illustrated) of the therapeutic device 10. When a start signal is received from the therapeutic device 10, the general controller 110 instructs the display controller 124, the target position identifier 140, and the output controller 150 to start a therapy, and the output controller 150 instructs the therapeutic device to capture the fluoroscopic image TI (Step S132). When the check box is unchecked in Step S126, even if no start signal is received from the therapeutic device 10, the general controller 110 may determine whether start imaging is instructed by operating the first button B1. When the target position PT identified by the target position identifier 140 is settled in the gating window, a gate-on signal may be output to the therapeutic device 10 (not illustrated). In this case, the beam B is not output from the therapeutic device. When the check box has not been unchecked in Step S126 but the check box is unchecked after start imaging is selected, a gate-on signal may be output in the middle of imaging (not illustrated). In this manner, in the interface image IM, the output controller 150 outputs a gate-on signal to the therapeutic device 10 on condition that an input operation of causing a default state to be a cancel state is acquired by the input operation acquirer 122. Accordingly, unintentional irradiation of the therapeutic beam B to the object P is suppressed, and reliability of a therapy can be enhanced. When making a template is completed, without requiring an ending operation of the preparation stage, the input operation acquirer 122 receives an instruction to start the irradiation stage of the therapeutic beam B. Accordingly, it is possible to improve operability of the medical apparatus 100.

The target position identifier 140 performs matching of the fluoroscopic image TI and the template, thereby identifying the target position PT. The output controller 150 causes a gate-on signal to be output to the therapeutic device 10 when the target position is settled in the gating window. The display controller 124 causes the input/display 120 to display a therapeutic image in which the target position or the gating window GW is superimposed on the fluoroscopic image TI. The therapeutic image is displayed in the regions A1-1 and A1-2. A therapy continues until stop imaging is selected by operating the first button B1 (Step S134). The medical apparatus 100 may end a therapy even when a signal of completing irradiation is received from the therapeutic device 10 or when a signal indicating that an operation of ending irradiation is conducted in the therapeutic device 10 is received from the therapeutic device 10. In this manner, the output controller 150 outputs an instruction for an operation to the imager (the radiation sources 12-1 and 12-2, and the detectors 13-1 and 13-2) of the therapeutic device 10, and a particular function (the target position identifier 140 or the like) of the medical apparatus 100 is activated in accordance with a unit-based input operation (an operation of the first button B1) acquired by the input operation acquirer 122. Accordingly, the medical apparatus 100 can manage an operation of the therapy system 1 including the therapeutic device 10 in an integrated manner, so that convenience is improved.

The display controller 124 may change the color of the gating window when a gate-on signal is output (in the preparation stage, when the conditions for outputting a gate-on signal are fulfilled) in the checking image and the therapeutic image. For example, regarding both the fluoroscopic images TI-1 and TI-2, the border line of the gating window GW may be displayed in a first color when the target position PT is not settled in the gating window GW, may be displayed in a second color when the target position PT is settled in the gating window GW in only one of both the fluoroscopic images TI-1 and TI-2, and may be displayed in a third color when the target position PT is settled in the gating window GW (that is, when the conditions for outputting a gate-on signal are fulfilled) in both the fluoroscopic images TI-1 and TI-2. An error icon may be displayed when the target position PT is not settled in the gating window GW in both the fluoroscopic images TI-1 and TI-2.

When the conditions for outputting a gate-on signal are fulfilled, the display controller 124 may change the hue or the brightness of any of an inner region and an outer region of the gating window GW. Moreover, the medical apparatus 100 may include a notifier that issues notification by a sound or a vibration when the conditions for outputting a gate-on signal are fulfilled.

The mode switching between markerless tracking, marker tracking, and external respiratory synchronization may be received at an arbitrary timing over a period from the preparation stage to the therapy stage, instead of being received in only the processing of Step S100 in the foregoing flowchart. Suitably, redoing of processing is received. For example, in a scene displaying the checking image, an operation for redoing the processing from the step of capturing a template image is received. Accordingly, a trouble- some operation is no longer required, so that convenience can be improved. When the mode switching is performed after the fluoroscopic image TI is captured, the fluoroscopic image TI which has already been captured may be employed as a template.

Figure 6:
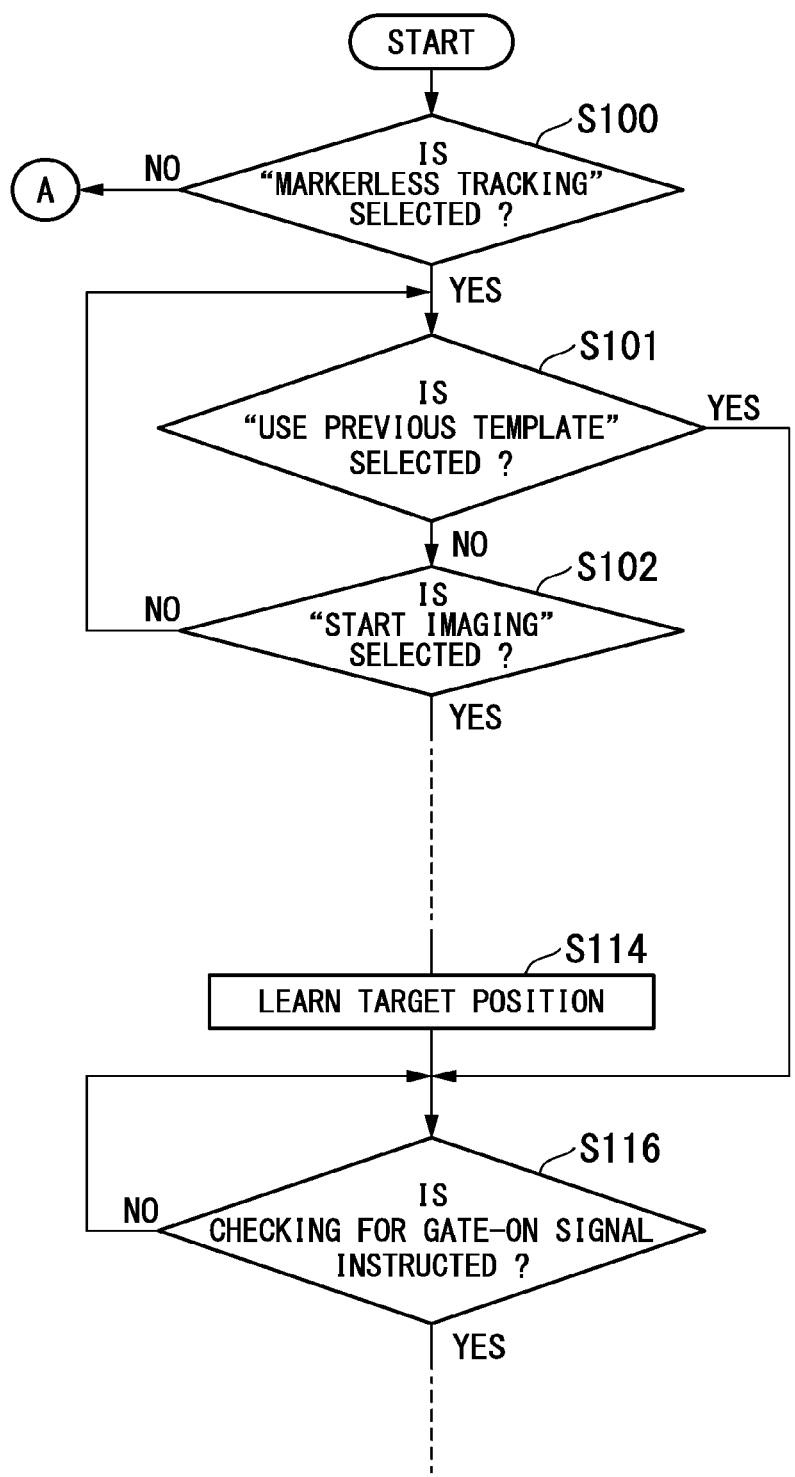
FIG. 6 is a flowchart (Part 2) illustrating an example of a flow of processing executed by the medical apparatus.

When a therapy is performed in a divided manner over a plurality of times, the therapy may be performed by succeeding a template made before a previous therapy. FIG. 6 is a flowchart (Part 2) illustrating an example of a flow of processing executed by the medical apparatus 100. As illustrated in the diagram, after markerless tracking is selected in the selection window SW, the general controller 110 determines whether or not "use previous template" is selected in any of the regions (Step S101). When "use previous template" is selected, the processing skips Steps S102 to S114, and the processing proceeds to Step S116. Accordingly, convenience is improved, and reliability of a therapy is improved.

In the medical apparatus 100, when a therapy is performed in a divided manner over a plurality of times, a DRR image made after the planning stage may be able to be repetitively used. Moreover, the medical apparatus 100 may be able to repetitively use a DRR image which has already been made even when the mode is switched.

The processing of the flowchart in FIG. 3 is based on the premise that template matching is performed. However, when a target position is identified through machine learning, the processing of Steps S112 and S114 is substituted with processing of learning a classifier which derives out a target position when a reference image is input.

A reference image is made before a therapy made. Moreover, the fluoroscopic image TI captured during a therapy may be added to a reference image in parallel. When machine learning is performed, machine learning may be performed in real time by utilizing the fluoroscopic image TI during a therapy.

<Flow of Therapy (Mode 2)>

Hereinafter, Mode 2 will be described. In Mode 2, the position of a lesion is identified by using a marker. A marker is embedded in the vicinity of a lesion, and the positional relationship between the marker and the lesion is learned in the planning stage. The marker is handled as a target position and is irradiated with the therapeutic beam B when the marker is settled in the gating window.

[Planning Stage]

In the planning stage of Mode 2, first, CT imaging of the object P is performed, and 4D CT images including n CT images are stored in the storage 160. Next, a physician, a radiologist, or the like inputs the contour to one CT image of the n CT images, for example. Next, for example, the image processor 136 sets the contour to each of the n CT images through deformable registration. Similar to Mode 1, the therapeutic plan is decided.

[Positioning Stage]

In the positioning stage, the bed position is adjusted. This is similar to that of Mode 1. Before CT imaging, one or more markers are embedded in the vicinity of a lesion in the body of the object P. The marker is formed of a material through which an X-ray is unlikely to be transmitted (for example, gold or platinum). Therefore, the marker appears black in the fluoroscopic image TI. For example, the marker has a shape of a sphere or a cylinder with a diameter of approximately 2 mm.

[Preparation Stage]

Figure 7:
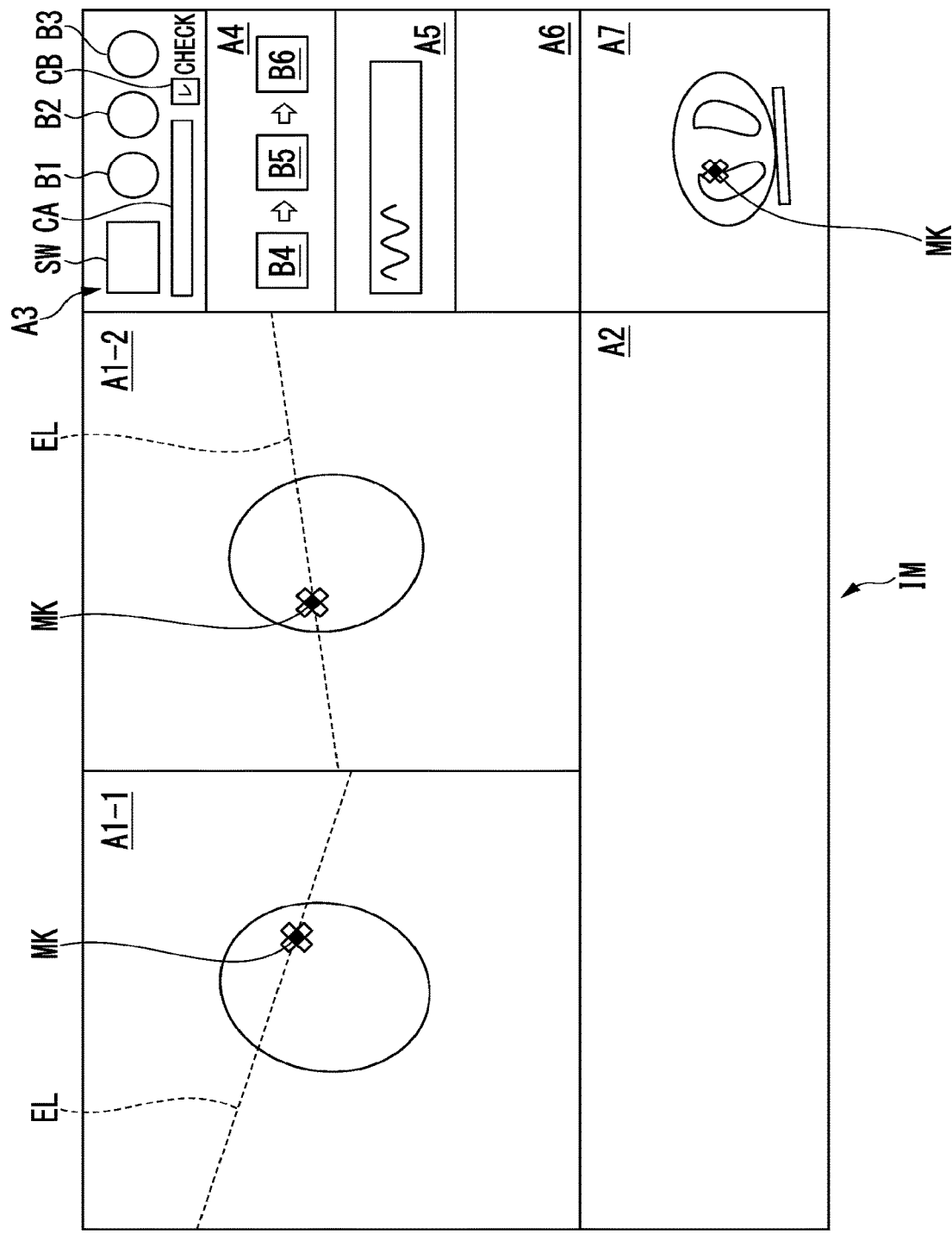
FIG. 7 is a view illustrating an example of a screen when a marker is selected.

In the preparation stage, a marker to be used for tracking by a physician or the like is selected on a CT image, on a DRR image, or on the fluoroscopic image TI of a certain respiratory phase. For example, the marker may be selected in the planning stage before the preparation stage. In this case, the position of a marker recognized by the image processor 136 in a CT image is displayed in the region A7, for example. FIG. 7 is a view illustrating an example of a screen when a marker is selected. In the illustrated screen, a DRR image is displayed in the regions A1-1 and A1-2, and a cross section of a CT image is displayed in the region A7. The fluoroscopic image TI may be displayed in place of a DRR image. The medical apparatus 100 receives designation of a marker MK through the following three methods. In the diagram, only one marker MK is displayed in each region. However, a plurality of markers MK are actually displayed to be able to be selected.

(1) A physician or the like designates the marker MK in the region A7. In accordance with this, an epipolar line EL is displayed on the fluoroscopic image TI. The marker MK on the epipolar line EL can be designated. When the marker MK on the epipolar line EL is designated, designation of the marker MK is completed.

(2) A physician or the like can also designate the marker MK on DRR images. In this case, when the marker MK is designated on one DRR image (for example, an image in the region A1-1), the epipolar line EL is displayed on another DRR image (for example, an image in the region A1-2). The marker MK on the epipolar line EL on another DRR image can be designated. When the marker MK on the epipolar line EL is designated, designation of the marker MK is completed. In this case, the position of the designated marker MK is displayed on a CT image.

(3) A physician or the like can also register the marker position as the marker ROI in the planning stage. In this case, the marker position may be displayed on DRR images of the regions A-1 and A1-2 and on a CT image of the region A7, and the marker MK to be used for tracking may be designated.

In the preparation stage, processing of deploying the position on a CT image, in which a marker is selected, in a CT image of another respiratory phase is performed (calculating the marker position of each phase). When the phase and the margin to be set to the gating window GW are designated, for example, the output controller 150 sets a region, in which a margin is applied to the position of the marker MK of each phase, to the gating window GW. The trajectory of the gating window GW or the marker MK may be displayed on a DRR image. The gating window may be set at any timing during a period from when a therapeutic plan is established until a therapy is performed.

Next, the fluoroscopic images TI of the object P for one or more respirations are captured. In this case, when detecting a marker is instructed, the target position identifier 140 detects the position of the marker MK on the fluoroscopic image TI and instructs the display controller 124 to cause the input/display 120 to display an image showing the detected position. A physician or the like checks that the position of the marker MK displayed by the input/display 120 coincides with the image showing the detected position.

In this case, regarding both the fluoroscopic images TI-1 and TI-2, the output controller 150 determines whether or not the target position (the positive correction amount of the position of a marker) is settled within the gating window. In the therapy stage, a gate-on signal is output to the therapeutic device 10 when the target position is settled within the gating window. However, in the preparation stage, the presence or absence of an output of a gate-on signal is transmitted to the display controller 124 via the general controller 110. The display controller 124 causes the input/display 120 to display the presence or absence of an output of a gate-on signal in parallel with displaying of a moving image. As a result, the output timing of a gate-on signal is checked by a physician or the like.

[Therapy Stage]

In the therapy stage, regarding both the fluoroscopic images TI-1 and TI-2, the output controller 150 outputs a gate-on signal to the therapeutic device 10 when the target position is settled within the gating window. Accordingly, a therapy is performed by irradiating a lesion of the object P with the therapeutic beam B.

<Display Image and Flowchart (Mode 2)>

Hereinafter, processing of the medical apparatus 100 for supporting the flow of the therapy described above will be described.

Figure 8:
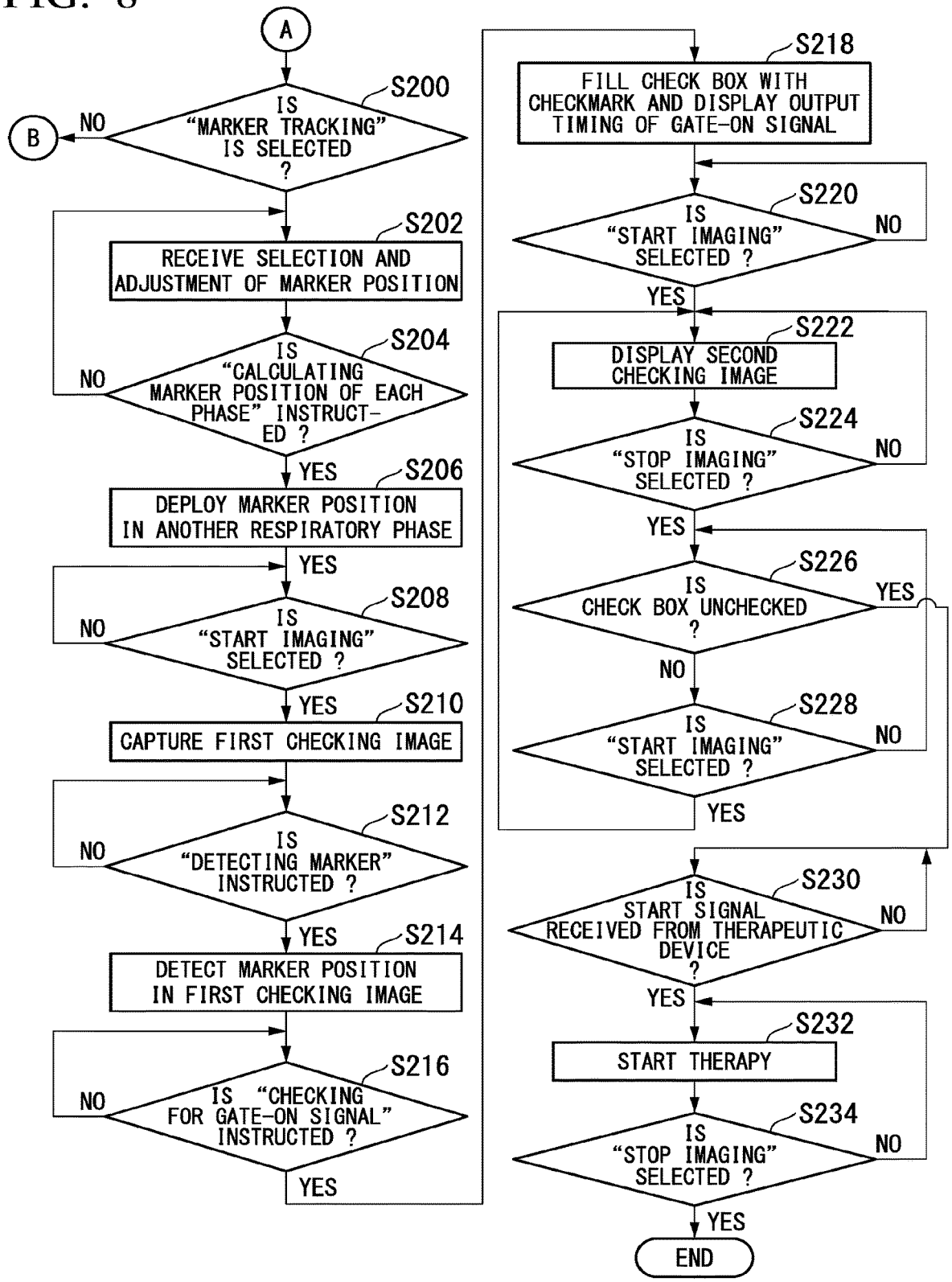
FIG. 8 is a flowchart (Part 3) illustrating an example of a flow of processing executed by the medical apparatus.

Hereinafter, various functions of the interface image IM will be described with reference to the flowchart. FIG. 8 is a flowchart (Part 3) illustrating an example of a flow of processing executed by the medical apparatus 100. First, with reference to the information input from the input operation acquirer 122, the general controller 110 determines whether or not marker tracking is selected in the selection window SW (Step S200). When a mode other than marker tracking is selected, the processing returns to Step S100 in the flowchart of FIG. 3.

Figure 9:
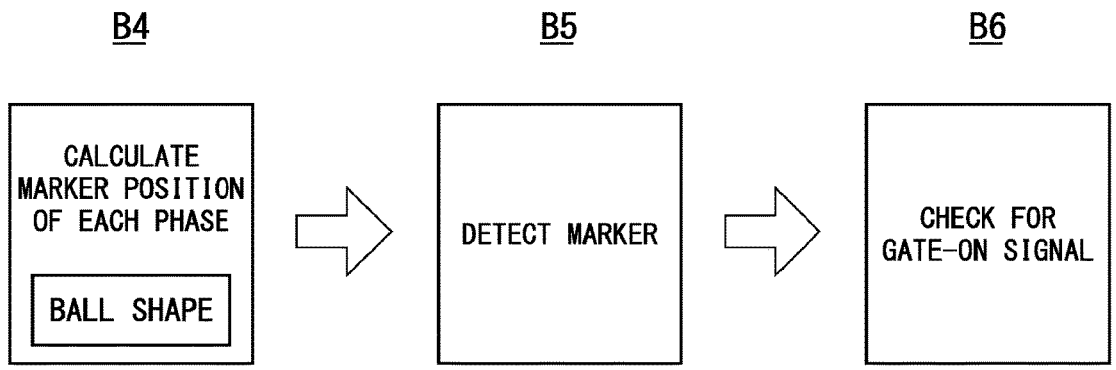
FIG. 9 is a view illustrating details of the fourth button, the fifth button, and the sixth button in Mode 2.

When marker tracking is selected in the selection window SW, the general controller 110 receives selection and adjustment of the position of a marker (Step S202). Processing in Steps S202 to S206 may be performed before marker tracking is selected in the selection window SW. In this case, the processing may skip Steps S202 to S206 through a manual operation or automatically. Next, the general controller 110 determines whether or not calculating the marker position of each phase is instructed by operating the fourth button B4 (Step S204). FIG. 9 is a view illustrating details of the fourth button B4, the fifth button B5, and the sixth button B6 in Mode 2. In Mode 2, the fourth button B4 receives an instruction for calculating the marker position of each phase, the fifth button B5 receives an instruction for detecting a marker, and the sixth button B6 receives an instruction for checking for a gate-on signal. In the fourth button B4, the shape of the marker can be designated.

When calculating the marker position of each phase is instructed by operating the fourth button B4, the general controller 110 instructs the image processor 136 to deploy the position of a marker in a CT image of a certain respiratory phase in another respiratory phase (Step S206). In this case, the display controller 124 causes the input/display 120 to display the marker region of interest (ROI) indicating the position of a marker in a CT image in the region A7 or the like.

Next, the general controller 110 determines whether or not start imaging is selected by operating the first button B1 (Step S208).

When start imaging is selected by operating the first button B1, the general controller 110 instructs the output controller 150 to instruct the therapeutic device 10 to capture the fluoroscopic image TI which will become a first checking image (Step S210). For example, the output controller 150 instructs the therapeutic device 10 to capture the fluoroscopic images TI fork times of respirations. The output controller 150 may output an instruction for ending imaging to the therapeutic device 10 when the first button B1 is operated again.

Next, the general controller 110 determines whether or not detecting a marker is instructed by operating the fifth button B5 (Step S212). When detecting a marker is instructed by the fifth button B5, the general controller 110 instructs a marker detecting unit 134 to detect the position of a marker in each of the first checking images captured in Step S204 (Step S214). The position of a marker detected by the marker detecting unit 134 is displayed in a manner of being superimposed on the first checking images reproduced as moving images in the regions A1-1 and A1-2, for example.

Next, the general controller 110 determines whether or not checking for a gate-on signal is instructed by operating the sixth button B6 (Step S216). When checking for a gate-on signal is instructed, the general controller 110 instructs the display controller 124 to change the check box CB into a state filled with checkmark and causes the input/display 120 to display the output timing of a gate-on signal (Step S218). In the state in which the check box CB is filled with checkmark, the output timing of a gate-on signal is calculated and displayed, but a gate-on signal is not actually output to the therapeutic device 10.

Next, the general controller 110 determines whether or not start imaging is selected by operating the first button B1 (Step S220). When start imaging is selected by operating the first button B1, the general controller 110 instructs the output controller 150 to instruct the therapeutic device 10 to capture the fluoroscopic image TI and instructs the display controller 124 to cause the input/display 120 to display a second checking image using the captured fluoroscopic image TI (Step S222).

The second checking image is displayed in the regions AI-1 and AI-2. The checking image is an image in which the target position PT or the gating window GW is superimposed on the fluoroscopic image TI which is reproduced as a moving image (refer to FIG. 2). The output controller 150 outputs a gate-on signal to the display controller 124, which displays the gate-on signal in the region A2 when the target position PT is settled in the gating window GW. A physician or the like can check for whether or not the target position PT such as a lesion of the object P is recognized as a correct position, whether or not the timing the target position PT is settled in the gating window GW is appropriate, the output efficiency of a gate-on signal, and the like, by visually recognizing this second checking image. The second checking image is displayed until stop imaging is selected by operating the first button B1 (Step S224). Even after stop imaging is selected, the checking image can be traced back and checked for by operating the control area CA in which the slide bar, the frame advancing switch, and the like are set.

When stop imaging is selected by operating the first button B1, the general controller 110 determines whether or not checkmark of the check box CB is canceled (check box CB is unchecked) (Step S226). When checkmark of the check box CB is not canceled, the general controller 110 determines whether or not start imaging is selected by operating the first button B1 (Step S228). When start imaging is selected, the processing returns to Step S222, and when start imaging is not selected, the processing returns to Step S226. When checkmark of the check box CB is canceled, the general controller 110 determines whether or not a start signal is received from the therapeutic device 10 (Step S230). This start signal is a signal output when the therapeutic device 10 can start a therapy by operating a switch (not illustrated) of the therapeutic device 10. When a start signal is received from the therapeutic device 10, the general controller 110 instructs the display controller 124, the marker detecting unit 134, the target position identifier 140, and the output controller 150 to start a therapy, and the output controller 150 instructs the therapeutic device to capture the fluoroscopic image TI (Step S232). When the check box is unchecked in Step S226, even if no start signal is received from the therapeutic device 10, the general controller 110 may determine whether start imaging is instructed by operating the first button B1. When the target position PT identified by the target position identifier 140 is settled in the gating window, a gate-on signal may be output to the therapeutic device 10 (not illustrated). In this case, the beam B is not output from the therapeutic device. When the check box has not been unchecked in Step S226 but the check box is unchecked after start imaging is selected, a gate-on signal may be output in the middle of imaging (not illustrated). The target position identifier 140 identifies the target position PT based on the position of a marker detected by the marker detecting unit 134. The output controller 150 causes a gate-on signal to be output to the therapeutic device 10 when the target position is settled in the gating window. The display controller 124 causes the input/display 120 to display a therapeutic image in which the target position or the gating window GW is superimposed on the fluoroscopic image TI. The therapeutic image is displayed in the regions A1-1 and A1-2. A therapy continues until stop imaging is selected by operating the first button B1 (Step S234). The medical apparatus 100 may end a therapy even when a signal of completing irradiation is received from the therapeutic device 10 or when a signal indicating that an operation of ending irradiation is conducted in the therapeutic device 10 is received from the therapeutic device 10.

The display controller 124 may change the color of the gating window when a gate-on signal is output (in the preparation stage, when the conditions for outputting a gate-on signal are fulfilled) in the second checking image and the therapeutic image. For example, regarding both the fluoroscopic images TI-1 and TI-2, the border line of the gating window GW may be displayed in a first color when the target position PT is not settled in the gating window GW, may be displayed in a second color when the target position PT is settled in the gating window GW in only one of both the fluoroscopic images TI-1 and TI-2, and may be displayed in a third color when the target position PT is settled in the gating window GW (that is, when the conditions for outputting a gate-on signal are fulfilled) in both the fluoroscopic images TI-1 and TI-2. An error icon may be displayed when the target position PT is not settled in the gating window GW in both the fluoroscopic images TI-1 and TI-2.

When the conditions for outputting a gate-on signal are fulfilled, the display controller 124 may change the hue or the brightness of any of an inner region and an outer region of the gating window GW. Moreover, the medical apparatus 100 may include a notifier that issues notification by a sound or a vibration when the conditions for outputting a gate-on signal are fulfilled.

The mode switching between markerless tracking, marker tracking, and external respiratory synchronization may be received at an arbitrary timing over a period from the preparation stage to the therapy stage, instead of being received in only the processing of Step S200 in the flowchart. Suitably, redoing of the processing is received. For example, in a scene displaying the checking image, an operation for redoing the processing from the step of imaging a template image is received.

Figure 10:
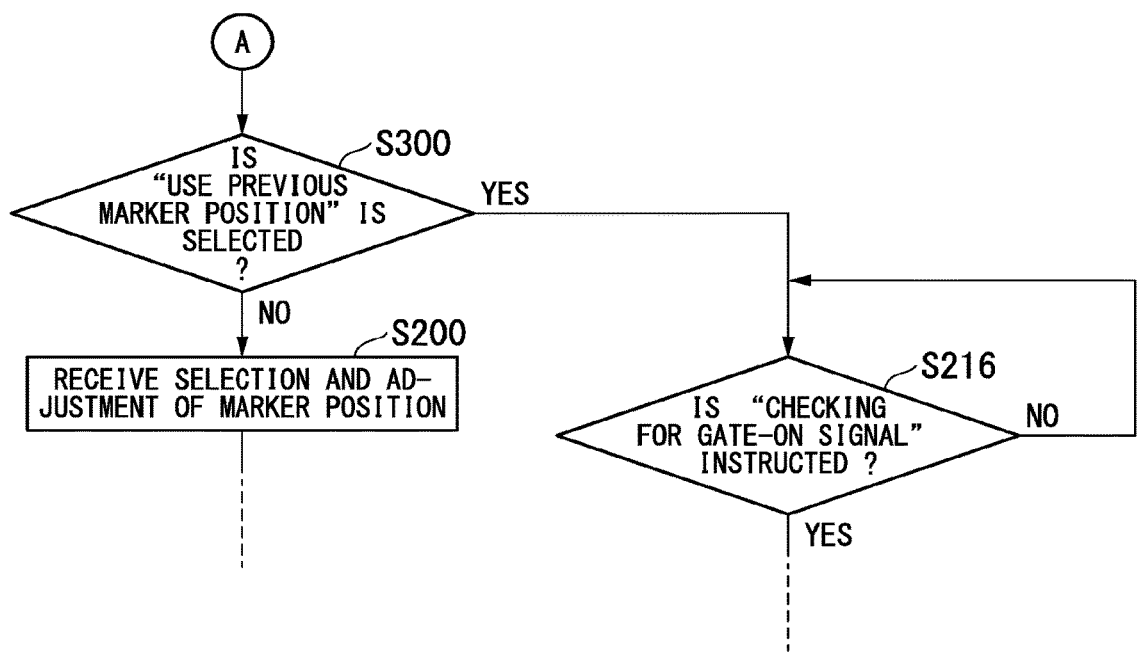
FIG. 10 is a flowchart (Part 4) illustrating an example of a flow of processing executed by the medical apparatus.

When a therapy is performed in a divided manner over a plurality of times, the therapy may be performed by succeeding the position of a marker selected and positionally adjusted before a previous therapy. FIG. 10 is a flowchart (Part 4) illustrating an example of a flow of processing executed by the medical apparatus 100. As illustrated in the diagram, after marker tracking is selected in the selection window SW, the general controller 110 determines whether or not "use previous marker position" is selected in any of the regions (Step S300). When "use previous marker position" is selected, the processing skips Steps S200 to S214, and the processing proceeds to Step S216.

<Mode 3>

Hereinafter, Mode 3 will be simply described.

[Planning Stage]

In the planning stage of Mode 3, first, CT imaging of the object P is performed. In CT imaging, images of the object P are captured in various directions for each of various respiratory phases. Next, 4D CT images are generated based on the results of the CT imaging. 4D CT images are n three-dimensional CT images arranged in time series. A period obtained by multiplying this number n by the time interval between the time-series images is set to cover a period in which the respiratory phase changes by one cycle, for example. 4D CT images are stored in the storage 160.

Next, a physician, a radiologist, or the like inputs a contour with respect to one CT image of n CT images, for example. This contour is a contour of a tumor which is a lesion or a contour of an organ which is not intended to be irradiated with the therapeutic beam B. Next, for example, the image processor 136 sets the contour for each of n CT images through deformable registration. Next, a therapeutic plan is decided. A therapeutic plan is a plan for regulating irradiation of the place, the direction, and the quantity of the therapeutic beam B in accordance with the position of a lesion based on information of the set contour. The therapeutic plan is decided in accordance with a therapeutic method such as the gated irradiation method or a tracking irradiation method. A part or all of the processing in the planning stage may be executed by an external device. For example, processing of generating 4D CT images may be executed by a CT device. A respiratory phase in which a lesion is irradiated with the therapeutic beam B is required when irradiation of the therapeutic beam B is performed in a direction decided in the therapeutic plan.

[Positioning Stage]

In the positioning stage, the bed position is adjusted. This is similar to that of Mode 1.

[Therapy Stage]

In the therapy stage, when a respiratory waveform (an external respiratory phase) grasped by the output controller 150 based on the output value of the sensor 15 is settled within the set irradiation range, irradiation of the therapeutic beam B is performed.

<Others>

The medical apparatus 100 of the foregoing embodiment may include a daemon program which is activated at all times. The medical apparatus 100 receives the results of the therapeutic plan described above from another device. The daemon program may automatically activate the function of each part of the medical apparatus 100 as the results of the therapeutic plan are received, as long as the therapeutic plan is a plan for internal respiratory synchronization or external respiratory synchronization. In this case, when the daemon program is a plan for internal respiratory synchronization, the daemon program may start preparation processing for tracking the target position such as deformable registration, and when the daemon program is a plan for external respiratory synchronization, the daemon program may display only the interface image IM.

Each step of processing in the flowchart illustrated in FIGS. 3, 6, 8, 10, and the like as an example may be subjected to an interlock such that the processing does not proceed unless positioning approval notification is received. The positioning approval notification may be issued in response to an input operation performed with respect to the input/display 120 or may be received from another device. Each step of processing in the flowchart illustrated in FIGS. 3, 6, 8, 10, and the like as an example may be controlled to return to the point of time positioning approval notification is received, when positioning approval cancellation notification is received.

When a therapy is performed over a plurality of times, the general controller 110 retains various pieces of data at the time of a therapy before a previous therapy (a template, a tracking result, a positioning approval history) in the storage 160, the display controller 124 may cause the input/display 120 to display a comparison with respect to therapeutic circumstances on the same day.

The medical apparatus 100 may retain each of the learning result obtained from only a DRR image, the learning result from a DRR image and the fluoroscopic image TI captured at the time of a therapy of the first day, and the learning result from a DRR image and the fluoroscopic image TI captured at the time of a therapy of the second day. Then, on the day of the therapy, the medical apparatus 100 may automatically or manually select one of the retained learning results and use the selected result for identifying the target position.

The medical apparatus 100 may retain each of the template used for a therapy of the first day, and the template used for a therapy of the second day. Then, on the day of the therapy, the medical apparatus 100 may automatically or manually select one of the retained templates and use the selected template for identifying the target position.

When the learning result or the template described above is automatically selected, the medical apparatus 100 may select information of a day indicating a trajectory closest to the trajectory of the tracking value on the day of the therapy.

According to at least one embodiment described above, it is possible to comprehensively support a therapy through internal respiratory synchronization by including an acquirer (130) that acquires a fluoroscopic image of the object P from an imager (12-1, 12-2, 13-1, 13-2) which performs imaging by irradiating the object P with an electromagnetic wave to generate the fluoroscopic image TI, an identifier (140) that identifies the target position PT of the object P in the fluoroscopic image TI, an output controller (150) that outputs a gate-on signal to a therapeutic device (10) which irradiates the object P with the therapeutic beam B when the target position PT identified by the identifier is settled within the gating window GW, a display controller (124) that causes a display (120) to display the interface image IM for receiving an instruction to start each of a preparation stage of a therapy and an irradiation stage of the therapeutic beam B, and an input operation acquirer (122) that receives an input operation performed by a user in the interface image IM.

The foregoing embodiment can be expressed as follows.

A medical apparatus is configured to include a hardware processor, and a storage device that stores a program.

The hardware processor executes the program to acquire a fluoroscopic image of a object from an imager which performs imaging by irradiating the object with an electromagnetic wave to generate the fluoroscopic image, identify a target position of the object in the fluoroscopic image, output an irradiation permission signal to a therapeutic device which irradiates the object with a therapeutic beam when the target position identified by the identifier is settled within an irradiation permission range, cause a display to display an interface image for receiving an instruction to start each of a preparation stage of a therapy and an irradiation stage of the therapeutic beam, and acquire details of an input operation performed by a user in the interface image.

The embodiment of the present invention has been described. However, the embodiment is presented merely as an example and is not intended to limit the scope of the invention. The embodiment can be performed in various other forms, and various omissions, replacements, and changes can be performed within a range not departing from the gist of the invention. The embodiment and a modification thereof are included in the invention disclosed in Claims and a range equivalent thereto in a manner similar to being included in the scope and the gist of the invention.

What is claimed is:

1. A medical apparatus comprising:
an acquirer configured to acquire a fluoroscopic image of an object from an imager which performs imaging by irradiating the object with an electromagnetic wave to generate the fluoroscopic image;
an identifier configured to identify a target position of the object in the fluoroscopic image;
an output controller configured to output an irradiation permission signal to a therapeutic device which irradiates the object with a therapeutic beam when the target position identified by the identifier is settled within an irradiation permission range;
a display controller configured to cause a display to display an interface image for receiving an instruction to start each of a preparation stage of a therapy and an irradiation stage of the therapeutic beam; and
an input operation acquirer configured to acquire details of an input operation performed by a user in the interface image.

2. The medical apparatus according to claim 1,
wherein the output controller is configured to output an instruction for an operation to the imager in accordance with the details of an input operation acquired by the input operation acquirer.

3. The medical apparatus according to claim 1,
wherein the output controller is configured to output an instruction for an operation to the imager and a particular function of the medical apparatus is activated, in accordance with a unit-based input operation acquired by the input operation acquirer.

4. The medical apparatus according to claim 1,
wherein the output controller is configured to output the irradiation permission signal to the therapeutic device on condition that an input operation of causing a default state to be a cancel state is received by the input operation acquirer after a predetermined input operation in the interface image.

5. The medical apparatus according to claim 1,
wherein the preparation stage of a therapy is a stage in which the identifier is configured to set a tracking condition for identifying the target position or a reference image is made, and
wherein the input operation acquirer is configured to receive an instruction to start the irradiation stage of the therapeutic beam without requiring an ending operation of the preparation stage.

6. The medical apparatus according to claim 1,
wherein when a therapy is performed over a plurality of times, information used by the identifier for identifying the target position, which is information designated through learning or by the user is succeeded.

7. The medical apparatus according to claim 6,
wherein the succeeded information includes a position of a lesion designated in three-dimensional volume data.

8. The medical apparatus according to claim 6,
wherein the succeeded information includes a position of a selected marker.

9. The medical apparatus according to claim 1,
wherein the display controller is configured to cause the display to display the irradiation permission range in a manner of being superimposed on the fluoroscopic image and changes a color of the irradiation permission range when the irradiation permission signal is output.

10. The medical apparatus according to claim 1,
wherein the display controller is configured to cause the display to display the irradiation permission range in a manner of being superimposed on the fluoroscopic image and changes a hue or brightness of any of an inner region or an outer region of the irradiation permission range when the irradiation permission signal is output.

11. The medical apparatus according to claim 1, further comprising:
a notifier configured to issue notification by a sound or a vibration when the irradiation permission signal is output.

12. The medical apparatus according to claim 1,
wherein,
after the interface image for receiving an instruction to start the preparation stage of the therapy is operated, the identifier identifies the target position of the object in the fluoroscopic image, and the display controller causes the display to display the target position and the irradiation permission range on the fluoroscopic image, and
when the interface image for receiving an instruction to start the irradiation stage of the therapeutic beam is operated, the output controller can output the irradiation permission signal to the therapeutic device.

13. A medical apparatus comprising:
an acquirer configured to acquire a fluoroscopic image of an object from an imager which performs imaging by irradiating the object with an electromagnetic wave to generate the fluoroscopic image;
an identifier configured to identify a target position of the object in the fluoroscopic image;
an output controller configured to output an irradiation permission signal to a therapeutic device which irradiates the object with a therapeutic beam when the target position identified by the identifier is settled within an irradiation permission range;
a display controller configured to cause a display to display an interface image for receiving an instruction to start each of a preparation stage of a therapy and an irradiation stage of the therapeutic beam; and
an input operation acquirer configured to acquire details of an input operation performed by a user in the interface image,
wherein the input operation acquirer is configured to acquire a switching operation between marker tracking and markerless tracking in the preparation stage of a therapy and the irradiation stage of the therapeutic beam.

14. A method executed by a medical apparatus, comprising;
- acquiring a fluoroscopic image of an object from an imager which performs imaging by irradiating the object with an electromagnetic wave to generate the fluoroscopic image,
- identifying a target position of the object in the fluoroscopic image,
- outputting an irradiation permission signal to a therapeutic device which irradiates the object with a therapeutic beam when the identified target position is settled within an irradiation permission range,
- causing a display to display an interface image for receiving an instruction to start each of a preparation stage of a therapy and an irradiation stage of the therapeutic beam, and
- acquiring details of an input operation performed by a user in the interface image.

15. The method according to claim 14, wherein,
- after the interface image for receiving an instruction to start the preparation stage of the therapy is operated, the target position of the object in the fluoroscopic image is identified, and the target position and the irradiation permission range are displayed on the fluoroscopic image by the display, and
- when the interface image for receiving an instruction to start the irradiation stage of the therapeutic beam is operated, the irradiation permission signal can be output to the therapeutic device.

* * * * *